United States Patent
Kadlec et al.

(10) Patent No.: US 6,770,708 B2
(45) Date of Patent: Aug. 3, 2004

(54) SILICONE ELASTOMERS COMPOSITIONS

(75) Inventors: Donald Anthony Kadlec, Midland, MI (US); Zuchen Lin, Midland, MI (US); William James Schulz, Jr., Midland, MI (US); Janet Mary Smith, Swarz Creek, MI (US); Michael Stephen Starch, Midland, MI (US); Shizhong Zhang, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/229,739

(22) Filed: Aug. 27, 2002

(65) Prior Publication Data

US 2004/0044121 A1 Mar. 4, 2004

(51) Int. Cl.[7] .............................................. C08L 83/04
(52) U.S. Cl. ......................... 524/588; 528/31; 528/32; 528/25; 556/445; 424/65; 424/70.1; 424/78.02
(58) Field of Search .............................. 524/588; 528/31, 528/32, 25; 556/445; 424/65, 70.1, 78.02

(56) References Cited

U.S. PATENT DOCUMENTS

| | | | |
|---|---|---|---|
| 5,654,362 A | 8/1997 | Schulz, Jr. et al. ......... | 524/862 |
| 5,833,973 A | 11/1998 | Dobkowski et al. ...... | 424/18.08 |
| 5,849,314 A | 12/1998 | Dobkowski et al. ........ | 424/401 |
| 5,919,468 A | 7/1999 | Bara ........................... | 424/401 |
| 5,959,018 A * | 9/1999 | Miyake et al. | |
| 5,977,280 A * | 11/1999 | Kadlec et al. | |
| 6,200,581 B1 | 3/2001 | Lin et al. ..................... | 424/401 |
| 6,388,005 B1 * | 5/2002 | Morita et al. | |
| 2002/0032270 A1 * | 3/2002 | Azechi | |

FOREIGN PATENT DOCUMENTS

| | | | | |
|---|---|---|---|---|
| EP | 0 917 870 A1 | 11/1997 | ............ | A61K/7/48 |
| EP | 0 852 945 B1 | 12/1997 | ............ | A61K/7/48 |
| EP | 0 908 175 A1 | 9/1998 | ............ | A61K/7/48 |
| EP | 0 869 142 A3 | 1/1999 | | |
| EP | 0 882 753 B1 | 1/2003 | | |
| WO | WO 97/44010 | 5/1997 | ............ | A61K/7/48 |
| WO | WO 98/00105 | 6/1997 | ............ | A61K/7/48 |
| WO | WO 98/35649 | 3/1998 | ............ | A61K/7/42 |
| WO | WO 98/42307 | 3/1998 | ............ | A61K/7/48 |
| WO | WO 99/43297 | 2/1999 | ............ | A61K/7/48 |
| WO | WO 99/51192 | 3/1999 | ............ | A61K/7/00 |
| WO | WO 03/064533 A1 | 8/2003 | | |

* cited by examiner

Primary Examiner—Kuo-Liang Peng
(74) Attorney, Agent, or Firm—Sharon K. Severance; Alan Zombeck

(57) ABSTRACT

This invention is directed to an elastomer composition produced by crosslinking a high molecular weight $\equiv$Si—H containing polysiloxane and a diene, diyne or ene-yne compound in the presence of a diluent. The elastomer composition is suitable for use in forming personal care compositions.

30 Claims, No Drawings

SILICONE ELASTOMERS COMPOSITIONS

FIELD OF THE INVENTION

This invention is directed to an elastomer composition produced by cross-linking a high molecular weight ≡Si—H containing polysiloxane and a diene, diyne or ene-yne compound in the presence of a diluent. The elastomer composition is suitable for use in forming personal care compositions.

BACKGROUND OF THE INVENTION

Cross-links are junctions of polymer strands in a three-dimensional network. They may be viewed as long-chain branches that are so numerous that a continuous insoluble network or gel is formed.

Increasingly, platinum catalyzed hydrosilylation reactions are being used to form networks. They typically involve reactions between a low molecular weight polysiloxane containing several ≡Si—H groups, and a high molecular weight polysiloxane containing several ≡Si-vinyl groups, or vice versa.

Attractive features of this mechanism are that (i) no by-products are formed, (ii) cross-linking sites and hence network architecture can be narrowly defined, and (iii) hydrosilylation will proceed even at room temperature to form the networks. In the mechanism, crosslinking involves addition of ≡SiH across multiple bonds, i.e., ≡SiH+CH$_2$=CH—R→≡SiCH$_2$CH$_2$—R.

U.S. Pat. No. 5,654,362 also disclosed a method of making silicone elastomers comprising (A) an ≡Si—H containing polysiloxane of formula R$_3$SiO(R'$_2$SiO)$_a$(R"HSiO)$_b$SiR$_3$ and optionally an ≡Si—H containing polysiloxane of formula HR$_2$SiO(R'$_2$SiO)$_c$SiR$_2$H or formula HR$_2$SiO(R'$_2$SiO)$_a$(R"HSiO)$_b$SiR$_2$H where R, R', and R" are alkyl groups of 1–6 carbon atoms; a is 0–250; b is 1–250; and c is 0–250; with (B) an alpha, omega-diene as only the unsaturated hydrocarbon of formula CH$_2$=CH(CH$_2$)$_x$CH=CH$_2$ where x is 1–20; conducting the reaction in the presence of a platinum catalyst and (C) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and continuing the reaction until a gel is formed by crosslinking and addition of ≡Si—H across double bonds in the alpha, omega-diene.

A need still exists, however, for new silicone elastomers to have improved properties. It has been found that by using a higher molecular weight ≡SiH containing polysiloxane, the elastomer composition comprised of silicone elastomers have unique sensory benefits, thickening efficiency, and/or reduced syneresis properties.

SUMMARY OF THE INVENTION

This invention relates to an elastomer composition comprising
(A) a silicone elastomer having a first polymeric unit of the average formula:

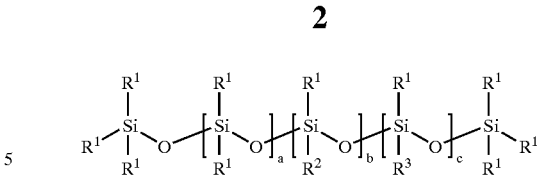

where each R$^1$ is independently a monovalent hydrocarbon group having 1 to 30 carbon atoms;
R$^2$ is a hydrogen (H) atom
R$^3$ is a cross-link —E—Y—E—, wherein one end of the cross-link is bonded to a second polymeric unit; each E is a divalent group selected from —CH$_2$CH$_2$— or —CH=CH— and Y is a divalent group that is a hydrocarbon, a siloxane or any combination of these; and
a is 265 to 2000, b is 0 to 249 and c is 1 to 250 with the provision that b+c≦250 and
(B) a diluent.

Another embodiment of this invention to provide a method for making an elastomer composition wherein the method comprises
(1) reacting in the presence of a hydrosilylation catalyst
   (a) a ≡Si—H containing polysiloxane having an average formula

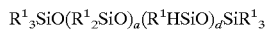

where each R$^1$ is independently a monovalent hydrocarbon group having 1 to 30 carbon atoms; a is 265 to 2000; and d is 1 to 250; with
   (b) a diene, diyne or ene-yne compound; wherein (a) and (b) are dispersed in
   (c) a diluent; and
(2) continuing the reaction until a silicone elastomer is formed by crosslinking and addition of ≡Si—H across unsaturated bonds in the diene, diyne or ene-yne compound.

In another embodiment of this invention, the elastomer composition is crumbled into a silicone powder using mechanical force.

In another embodiment of this invention, a base composition is formed by subjecting to a shear force a composition comprising (I) the elastomer composition and (II) a second diluent.

DETAILED DESCRIPTION OF THE INVENTION

This invention pertains to an elastomer composition comprising
(A) a silicone elastomer having a first polymeric unit of the average formula:

(I)

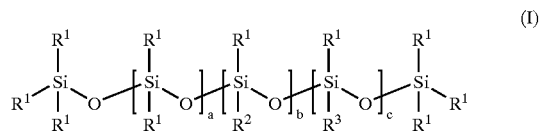

where each R$^1$ is independently a monovalent hydrocarbon group having 1 to 30 carbon atoms;
R$^2$ is a hydrogen (H) atom
R$^3$ is a cross-link —E—Y—E—, wherein one end of the cross-link bonded to a second polymeric unit; each E is a divalent group selected from —CH$_2$CH$_2$— or —CH=CH— and Y is a divalent group that is a hydrocarbon, a siloxane or any combination of these; and a is 265 to 2000 (alternatively 350 to 1000), b is 0 to 249 (alternatively 0 to 100) and c is 1 to 250 (alternatively 1 to 100) with the provision that b+c≦250 (alternatively ≦100) and (B) a diluent.

In the first polymeric unit $R^1$ is a monovalent hydrocarbon group having 1 to 30 carbon atoms. $R^1$ may be exemplified by, but not limited to, alkyl groups such as methyl, ethyl, propyl, butyl, pentyl, hexyl or isobutyl; aryl groups such as phenyl, biphenyl, naphthyl or anthracyl; alkaryl groups such as tolyl or xylyl; aralkyl groups such as benzyl, phenylethyl or 2-phenylpropyl, or polyether.

In the first polymeric unit, $R^3$ is a crosslink of the formula —E—Y—E— where each E is a divalent group independently selected from —CH$_2$CH$_2$— or —CH=CH—. Typically each E is —CH$_2$CH$_2$— and Y is a hydrocarbon group having 1 to 30 carbon atoms alternatively 1 to 10 carbon atoms. In the cross-link Y is a divalent group that is a hydrocarbon, a siloxane or any combination of these. When Y is a siloxane it typically has the formula

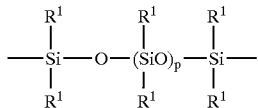

where $R^1$ is as previously defined and p is 0 to 20,000, alternatively 0 to 500.

$R^3$ may be exemplified by, but not limited to, polyether, pentylene, hexylene, heptylene, octylene, nonylene, decylene, dodecylene, tetradecylene and mixtures thereof.

One end of $R^3$ is bonded into the first polymeric unit shown in formula (I). The other end of $R^3$ is bonded to a second polymeric unit having the formula (≡Si—O$_{1/2}$) wherein the remaining two bond sites on the Si in this unit may be oxygen, $R^1$ or any combination thereof. The second polymeric unit may be the same as or different from polymeric unit (I). Typically the other end of $R^3$ is bonded into a second polymeric unit having the formula (II):

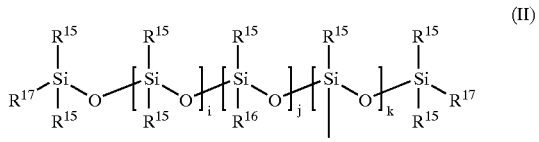

(II)

wherein each $R^{15}$, $R^{16}$, and $R^{17}$ is independently selected from hydrogen or a monovalent hydrocarbon group having 1 to 30 carbon atoms; and i is 0 to 2000, j is 0 to 250 and k is 1 to 250.

$R^{15}$, $R^{16}$ and $R^{17}$ may be exemplified by, but not limited to hydrogen, alkyl groups such as methyl, ethyl, propyl, butyl, pentyl, hexyl or isobutyl; aryl groups such as phenyl, biphenyl, naphthyl or anthracyl; alkaryl groups such as tolyl or xylyl, or aralkyl groups such as benzyl, phenylethyl or 2-phenylpropyl, or polyether.

The amount of cross-link in the silicone elastomer is from 0.01 to 90 mole %, alternatively 1 to 20 mole %.

The silicone elastomer typically contains from 10 to 40,000 of the total polymeric units (e.g. first and second polymeric units).

The elastomer composition of the instant invention also comprises a diluent (B). Suitable examples of diluents include silicones, both linear and cyclic (other than those used to prepare corresponding silicone elastomer (A)), organic oils, organic solvents and mixtures of these. Specific examples of diluents may be found in U.S. Pat. No. 6,200,581, which is hereby incorporated by reference for this purpose. Non-reactive or relatively non-reactive diluents are preferred. For purposes here, non-reactive is used in reference to the associated cross-linking reaction and used relative to the (other) reactants therein. A relatively non-reactive diluent would be less than one tenth as reactive with the other reactants as the others are with each other in the associated cross-linking reaction. The weight ratio range for (A):(B) is typically 1:100 to 10:1, alternatively 1:50 to 2:1, alternatively 1:20 to 1:1.

The elastomer compositions are prepared by a reacting, in the presence of a hydrosilylation catalyst, (a) a ≡Si—H containing polysiloxanes of formula $R^1_3SiO(R^1_2SiO)_a(R^1HSiO)_dSiR^1_3$ wherein each $R^1$ is independently a monovalent hydrocarbon group having 1 to 30 carbon atoms; a is 265 to 2000 (alternatively 350 to 1000); and d is 1 to 250 (alternatively 1 to 100) with (b) a diene, diyne or ene-yne compound; wherein (a) and (b) are dispersed in (c) a diluent. The reaction is continued until an elastomer is formed by crosslinking and addition of ≡Si—H across double bonds in the diene, diyne or ene-yne compound.

The ≡Si—H containing polysiloxane (a) is represented by compounds of the formula $R^1_3SiO(R^1_2SiO)_a(R^1HSiO)_dSiR^1_3$ where $R^1$, a and d are as defined previously (herein referred to as ≡Si—H containing polysiloxane (a')). In the ≡Si—H containing polysiloxane there is typically at least 20 ($R^1_2SiO$) units for every ($R^1HSiO$) unit (i.e. a:d ≧20:1), alternatively there are at least 35 ($R^1_2SiO$) units for every ($R^1HSiO$) unit, alternative there are at least 75 ($R^1_2SiO$) units for every ($R^1HSiO$) unit.

In addition (a) may contain compounds of the formula $HR^1_2SiO(R^1_2SiO)_eSiR^1_2H$ and/or the formula $HR^1_2SiO(R^1_2SiO)_a(R^1HSiO)_dSiR^1_2H$ (collectively referred to as ≡Si—H containing polysiloxane (a")) where $R^1$, a and d are as previously defined; and e is 0 to 250 (alternatively 0 to 100). The molar ratio of compounds a": a' in (a) is 0 to 20, alternatively 0 to 5. The ≡Si—H containing polysiloxane can be a single polysiloxane or a mixture of polysiloxanes.

Component (b) is a diene, diyne or ene-yne compound. Diene, diyne or ene-yne compounds are those compounds wherein there are at least two aliphatic unsaturated groups with some separation between the groups. Structurally, component (b) would (in the "alpha, omega diene" case) look something like HC=C—Y—C=CH, where Y is a divalent group that is a hydrocarbon, siloxane or any combination of these. The unsaturation could be at an end or pendant if part of a polymer molecule. Component (b) can be a single diene, diyne or ene-yne compound or a mixture of compounds.

Component (b) may be exemplified by, but not limited to, $E^1$—Y—$E^1$ where each $E^1$ is independently $CH_2$=CH— or CH≡C— and Y is as defined above and a siloxane containing two $E^1$—Y—E— groups.

Component (b) may be further exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3 butadiyne, 1, 5 hexadiyne (dipropargyl), and 1-hexene-5-yne.

A catalyst is required to effect the reaction between the ≡Si—H containing polysiloxane (a) and the diene, diyne or ene-yne compound (b). Suitable catalysts are Group VIII transition metals, i.e., the noble metals. Such noble metal catalysts are described in U.S. Pat. No. 3,923,705, incorporated herein by reference for its teaching of platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing about one-weight percent of platinum in a solvent such as toluene. Another preferred platinum catalyst is a reaction product of chloroplatinic acid and an organosilicon compound containing terminal aliphatic unsaturation. This platininum catalyst is described in U.S. Pat. No. 3,419,593 incorporated herein by reference. The noble metal catalysts are used in amounts from 0.00001 to 0.5 parts per 100 weight parts of the $\equiv$SiH containing polysiloxane, alternatively 0.00001 to 0.02 parts, and alternatively 0.00001–0.002 parts.

Components (a) and (b) are dispersed in a diluent (c). Diluent (c) is typically selected from (i) silicones, (ii) organic compounds, and (iii) mixtures of organic compounds and silicones. Diluent (c) is the same as diluent (B) described above.

Silicone diluents (i) include low molecular weight linear or cyclic volatile silicones, non-volatile alkyl or aryl silicones, and low molecular weight linear or cyclic functional silicones. The silicone may be a single silicone or a mixture of silicones. Typically the silicone is a low molecular weight volatile methyl silicone (VMS).

VMS compounds correspond to the average unit formula $(CH_3)_xSiO_{(4-x)/2}$ in which x has an average value of 2 to 3. Representative units in VMS compounds are $(CH_3)_3SiO_{1/2}$ units and $(CH_3)_2SiO_{2/2}$ units. Additionally there may be $CH_3SiO_{3/2}$ units and/or $SiO_{4/2}$ units that result in the formation of branched linear or cyclic volatile methyl silicones. Linear VMS have the formula $(CH_3)_3SiO\{(CH_3)_2SiO\}_ySi(CH_3)_3$ where y is 0 to 5. Cyclic VMS have the formula $\{(CH_3)_2SiO\}_z$ where z is 3 to 6. Typically these volatile methyl silicones have boiling points less than about 250° C. and viscosities of 0.65 to 5.0 centistokes (mm²/s).

Linear volatile methyl silicones may be further exemplified by, but not limited to, hexamethyldisiloxane, octamethyltrisiloxane, decamethyltetrasiloxane, dodecamethylpentasiloxane, tetradecamethylhexasiloxane; and hexadecamethylheptasiloxane. Cyclic volatile methyl silicones may be further exemplified by, but not limited to, hexamethylcyclotrisiloxane; octamethylcyclotetrasiloxane, decamethylcyclopentasiloxane, and dodecamethylcyclohexasiloxane. Branched volatile methyl silicones may be exemplified by, but not limited to, heptamethyl-3-{(trimethylsilyl)oxy}trisiloxane; hexamethyl-3,3,bis{(trimethylsilyl)oxy}trisiloxane; and pentamethyl {(trimethylsilyl)oxycyclotrisiloxane.

Linear poly alkyl or aryl silicones may be exemplified by, but not limited to, compounds of the formula $R^4_3SiO(R^4_2SiO)_mSiR^4_3$, and cyclic poly alkyl or aryl silicones are compounds of the formula $(R^4_2SiO)_n$ where $R^4$ is an alkyl group of 1–6 carbon atoms, or an aryl group such as phenyl, m has a value of 0 to 80, preferably 0 to 20 and n has a value of 0 to 9, preferably 4 to 6. These silicones have viscosities generally in the range of about 1–100 centistokes (mm²/s). Other representative low molecular weight non-volatile silicones have the general structure $R^5_3SiO(R^5R^6SiO)_pSiR^5_3$ where p has a value to provide polymers with a viscosity in the range of about 100 to 10,000 centistokes (mm²/sec) and $R^5$ and $R^6$ are alkyl radicals of 1–30 carbon atoms, or an aryl group such as phenyl. Typically, the value of p is about 80–375. Non-volatile polysiloxanes may be exemplified by, but not limited to, polydimethylsiloxane, polydiethylsiloxane, polymethylethylsiloxane, polymethylphenylsiloxane, and polydiphenylsiloxane.

Low molecular weight functional silicones can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

Organic diluents (ii) include aromatic hydrocarbons, aliphatic hydrocarbons, alcohols, aldehydes, ketones, amines, esters, ethers, glycols, glycol ethers, alkyl halides, or aromatic halides. The organic diluents may be exemplified by alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

The organic diluents may also include acetonitrile, nitromethane, dimethylformamide, propylene oxide, trioctyl phosphate, butyrolactone, furfural, pine oil, turpentine, and m-creosol; volatile flavoring agents; and other useful flavoring agents including aldehydes and esters; volatile fragrances such as natural products and perfume oils.

The organic diluent can be a single compound or a mixture of compounds. Additionally, the diluent (c) can be a mixture of a siloxane and organic diluent.

Carrying out of the process is simply a matter of combining the $\equiv$SiH containing polysiloxane(s), the diene, diyne or ene-yne compound, the diluent, and the catalyst; and mixing these ingredients at room temperature until a gel is formed. Higher temperatures to speed up the process can be used, if desired. Typically the reaction is carried out at a temperature of 30° C. to 150° C., alternatively 50° C. to 90° C.

The process for making the silicone elastomers is typically carried out using approximately a 0.7 to 1.3 molar ratio of $\equiv$Si—H containing polysiloxane to diene, diyne or ene-yne compound. Typically the molar ratio is 0.8 to 1.2 parts $\equiv$Si—H containing polysiloxane (a) to diene, diyne or ene-yne compound (b). The diluent (c) is added in an amount to provide of 1 to 98 percent by weight, alternatively 5 to 50 percent by weight based on the weight of (a), (b) and (c).

The resulting elastomer composition can be crumbled into a silicone powder using mechanical force. By "mechanical force" it is meant any device that provide mechanical input to the elastomers, such as blender or a mixer. The resulting silicone powder will typically have a particle size of 0.01 to 10000 micrometer, alternatively 1 to 100 micrometer.

The silicone powder has the unique property of being easily rubbed-in on the skin, and silicone resins can be incorporated therein to improve the substantivity of formulations applied to the skin. These materials are ideal for use in cosmetics such as antiperspirants and deodorants.

The resulting silicone elastomers can be combined a second diluent under a shear force to form base composition suitable in use to form cosmetic compositions. Elastomers containing 5 to 98 weight percent of the second diluent are stable and form uniform pastes with a wide viscosity range. Second diluents include those described herein previously as the diluent.

To produce the base compositions the second diluent is added to the silicone elastomer, and the resulting mixture is subjected to shear force to form a paste. Any type of mixing and shearing equipment may be used to perform these steps such as a batch mixer, planetary mixer, single or multiple screw extruder, dynamic or static mixer, colloid mill, homogenizer, sonolator, or a combination thereof.

The base compositions have excellent properties including clarity, thixotropy, and shear thinning, and spread smoothly on the skin. They can be applied in cosmetic and medical products as the base oil.

The silicone elastomer, silicone powder and base compositions have particular value in the personal care products. Because of the unique volatility characteristics of the diluent component of these compositions, they can be used alone, or blended with other personal care product ingredients, to form a variety of personal care products.

Examples of personal care product ingredients include, but are not limited to, ester waxes, oils and fats of animal or vegetable origin, fatty alcohols, fatty acids, alkyl esters of fatty acids; hydrocarbon oils and waxes; water, organic solvents, perfumes, surfactants, oil-soluble vitamins, water-soluble vitamins, oil-soluble drugs, water-soluble drugs, actives, pharmaceutical compounds and others.

In particular, the silicone elastomers, silicone powders and base compositions are useful in antiperspirants and deodorants, since they leave a dry feel, and do not cool the skin upon evaporation. They are lubricious and will improve the properties of skin creams, skin care lotions, moisturizers, facial treatments such as ache or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they will function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water-soluble substances such as vitamins. When incorporated into sticks, gels, lotions, aerosols, and roll-ons, the elastomers impart a dry, silky-smooth, payout. When incorporated into cosmetics and other skin care compositions the elastomers impart a matifying effect.

In addition, the elastomers exhibit a variety of advantageous and beneficial properties such as clarity, shelf stability, and ease of preparation. Hence, they have wide application, but especially in antiperspirants, deodorants, in perfumes as a carrier, and for conditioning hair.

The invention also includes personal care products that include the silicone elastomer, silicone powder or base composition of the present invention previously described herein. This would include hair, skin and underarm care products, more specifically conditioners, moisturizers, body washes, cosmetic foundations, blushes, lipsticks, eye liners, mascaras, eye shadows, antiperspirants and deodorants. Other examples of products that can be made using the compositions of the present invention are the same as can be made from the materials disclosed in U.S. Pat. No. 6,200,581, which is hereby incorporated by reference for these examples.

The silicone elastomers powders and base compositions have uses beyond the personal care arena, including their use as a filler or insulation material for electrical cable, a soil or water barrier for in-ground stabilization, or as a replacement for epoxy materials used in coil-on-plug designs in the electronics industry. They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying rheological, physical, or energy absorbing properties of such phases in either their neat or finished condition In addition, the silicone elastomers, powders and base compositions are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Other variations may be made in compounds, compositions, and methods described herein without departing from the essential features of our invention. The forms of our invention are exemplary and not limitations on its scope as defined in the claims.

The following non-limiting examples re provided so that one skilled in the art may more readily understand the invention.

EXAMPLES

Example 1

1.74 g of an organopolysiloxane with the average structure $Me_3SiO(Me_2SiO)_{1024}(MeHSiO)_{26.2}SiMe_3$, 0.03 g of 1,5-hexadiene, and 8.30 g of decamethylcyclopentasiloxane were added into a jar. 0.05 of Karstedt's catalyst described above containing 1 wt % of Pt was added while the solution was stirred. The jar was place in an 80° C. oven. Gellation took place within 30 minutes. The gel was left in the oven for 2 hours, resulting in a clear, hard gel.

Example 2

51.31 g of an organopolysiloxane with the average structure $Me_3SiO(Me_2SiO)_{396}(MeHSiO)_4SiMe_3$, 0.30 g of 1,5-hexadiene, and 50.07 g of decamethylcyclopentasiloxane were charged into jar. 0.28 g Karstedt's catalyst was added while the solution was stirred. The jar was placed in an 80° C. oven. Gellation took place within one hour. The gel was left in the reactor for 3 hours, and then 25 g of the gel was swollen with 125 g of decamethylcyclopentasiloxane under a shear force. A uniform and transparent paste was obtained.

Example 3

97.23 g of an organopolysiloxane with the average structure $Me_3SiO(Me_2SiO)_{396}(MeHSiO)_4SiMe_3$, 3.45 g of 1,5- hexadiene, and 400.53 g of a 10% solution of $Me_3SiO(Me_2SiO)_{396}(MeRSiO)_4SiMe_3$ in decamethylcyclopentasiloxane were charged into ajar (R is —$CH_2CH_2CH_2O(CH_2CH_2O)_{18}(CH_2CH_2O)_{18}H$.). 1.09 g Karstedt's catalyst was added while the solution was stirred. The jar was placed in an 80° C. oven. Gellation took place within one hour. The gel was left in the oven for 3 hours producing an opaque gel.

Example 4

99.47 g of an organopolysiloxane with the average structure $Me_3SiO(Me_2SiO)_{368}(MeHSiO)_{3.65}SiMe_3$, 0.57 g of 1,5-hexadiene, and 300.33 g of decamethylcyclopentasiloxane were charged into jar. 0.79 g Karstedt's catalyst was added while the solution was stirred. The jar then was placed in an 80° C. oven. Gellation took place within one hour. The gel was left in the oven for 4 hours. 39.9 g of the resulting gel was swollen with 60.0 g of decamethylcyclopentasiloxane under a shear force. A uniform and transparent paste with a viscosity of 160,000 mPaS was obtained.

Comparative Example 1

83.98 g of an organopolysiloxane with the average structure $Me_3SiO(Me_2SiO)_{88}(MeHSiO)_6SiMe_3$, 3.07 g of 1,5-hexadiene, and 412.50 g of decamethylcyclopentasiloxane were charged into jar. 1.04 g Karstedt's catalyst was added while the solution was stirred. The jar then was placed in 80° C. oven. Gellation took place within one hour. The gel was left in the oven for 3 hours. 40.0 g of the resulting gel was swollen with 60.0 g of decamethylcyclopentasiloxane under a shear force. A uniform, hazy viscous fluid with a viscosity of 800 mPaS was obtained. This illustrates the thickening efficiency difference of a elastomer with lower molecular weight $\equiv$SiH containing siloxane and a elastomer with higher molecular weight $\equiv$SiH containing siloxane at the same elastomer concentration (7%).

Comparative Example 2

67.65 g of an organopolysiloxane with the average structure $Me_3SiO(Me_2SiO)_{249.2}(MeHSiO)_{15.8}SiMe_3$, 2.35 g of 1,5-hexadiene, and 280.0 g of decamethylcyclopentasiloxane were charged into jar. 0.67 g Karstedt's catalyst was added while the solution was stirred. The jar then was placed in a water bath maintained at 70°±5° C. Gellation took place within 10 minutes. The sample was placed in an oven maintained at 70°±5° C. for 3 hours. 49.5 g of the resulting gel was swollen with 40.5 g of decamethylcyclopentasiloxane under a shear force (11% elastomer concentration). A uniform and transparent paste with a viscosity of 10,600 mPaS was obtained.

Example 5

89.52 g of an organopolysiloxane with the average structure $Me_3SiO(Me_2SiO)_{265.54}(MeHSiO)_{2.46}SiMe_3$, 0.48 g of 1,5-hexadiene, and 210.0 g decamethylcyclopentasiloxane were charged into jar. 0.75 g Karstedt's catalyst was added while the solution was stirred. The jar then was placed in a water bath maintained at 80°±5° C. Gellation took place within 1 hour. The sample was placed in an oven maintained at 80°±5° C. for 3 hours. 40.0 g of the resulting gel was swollen with 60 g of decamethylcyclopentasiloxane under a shear force (11% elastomer concentration). A uniform and transparent paste with a viscosity of 177,600 mPaS was obtained.

Example 6

173.98 g of an organopolysiloxane with the average structure $Me_3SiO(Me_2SiO)_{396}(MeHSiO)_4SiMe_3$, 1.01 g of 1,5-hexadiene, and 325.23 g of decamethylcyclopentasiloxane were charged into jar. 1.27 g Karstedt's catalyst was added while the solution was stirred. The jar was placed in an 80° C. oven. Gellation took place within one hour. The gel was left in the reactor for 3 hours. 34.5 g of the resulting gel were swollen with 65.51 g of decamethylcyclopentasiloxane under a shear force. A uniform and transparent paste was obtained.

Example 7

Antiperspirant pastes were formulated with silicone elastomers made in Example 6 and Comparative Example 1 respectively, and the other ingredients shown in Table 1. The antiperspirant produced using the elastomer composition made in Example 6 exhibited a high degree of spreadability, smoothness, little or no residue, and dryness, among its beneficial properties.

TABLE 1

Antiperspirant Formulation

| Ingredient | Amount |
|---|---|
| C12–15 Alkyl Benzoate (Finsolv TN, Finetex, Inc.) | 3 parts |
| Elastomer composition Paste (Example 6 or Comparative Example 1) diluted with Decamethylpentasiloxane to make a paste containing 12% elastomer | 37.5 parts (equivalent to 4.5% silicone elastomer) |
| Antiperspirant Active, Aluminum-Zirconium Tetraclilorohydrex-Gly (REACH AZP 908 SUF) | 25 parts |
| A mixture of Dimethicone and Trisiloxane Silicone Elastomer Powder, Dimethicone/Vinyl Dimethicone Crosspolymer | 33.5 parts 1 part |

The viscosity of the antiperspirant formulated with the elastomer composition of Example 6 had a viscosity of 285,000 mPaS, whereas the viscosity of the antiperspirant formulated with the elastomer composition of Comparative Example 1 had a viscosity of 175,000 mPaS. The viscosity measurements were obtained using a Brookfield viscometer, model RDVII+equipped with a Helipath stand using spindle 93 and a speed of 2.5 rpm.

The antiperspirant pastes were also tested for syneresis (the tendency for oil to separate from the formulation during shelf-aging). To determine the relative tendency to exhibit syneresis, approximately 30 g. of each antiperspirant pastes was subjected to centrifugal stress by placing them into a 50 mL disposable centrifuge tube and then spinning them at 3000 rpm for 30 minutes in a bench-top centrifuge (International Equipment Corporation, model HSN-II). After removing the centrifuge tubes from the centrifuge, the tubes were tared on an electronic balance and the liquid that had collected on top of the sample was carefully removed using a pipette. The weight of the removed liquid was recorded and % syneresis was reported as follows: % syneresis=(wt. of weight of removed liquid/wt. of sample)× 100. The antiperspirant paste prepared with the elastomer composition described in Example 6 had a syneresis of 9.4%, while the antiperspirant paste prepared with the elastomer composition described in Comparative Example 1 had a syneresis of 25.0%.

Based on the results from the antiperspirant pastes, the elastomer composition of Example 6 was a more efficient thickener and gave less syneresis compared to the elastomer composition of Comparative Example 1.

Example 7

Skin Lotions were formulated with silicone elastomers made in Example 6 and Comparative Example 1, respectively, as shown in Table 2.

TABLE 2

Facial Moisturizer Formulations

| Ingredient | Amount |
| --- | --- |
| Phase A | |
| Elastomer composition (diluted to 7% elastomer using Cyclopentasiloxane) | 10 parts |
| Octyl Methoxycinnamamte | 5 parts |
| Polyacrylamide (and) C13–14 Isoparaffin (and) Laureth-7 (Sepigel 305, SEPPIC) | 3 parts |
| Phase B | |
| Deionized water | 77.7 parts |
| Glycerin | 4.0 parts |
| DM DM Hydantoin (Glydant, Lonza, Inc.) | 0.3 parts |

Ingredients in Phase A were combined and mixed until uniform. Ingredients in Phase B were combined and mixed until uniform. Phase A was added to Phase B with vigorous mixing until homogeneous. The facial moisturizer made with the elastomer composition of Example 6 and the facial moisturizer made with the elastomer composition of Comparative Example 1 both had a pleasant feel during application and after drying, although the skin feel of the former moisturizer was described as somewhat richer compared to the latter moisturizer. Also, the facial moisturizer made with the elastomer composition of Example 6 gave more of a glossy film on the skin compared to the facial moisturizer made with the elastomer composition of Comparative Example 1.

What is claimed is:

1. An elastomer composition comprising

A silicone elastomer having a first polymeric unit of the formula:

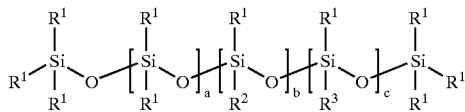

wherein each $R^1$ is independently a monovalent hydrocarbon group having 1 to 30 carbon atoms;

$R^2$ is a hydrogen (H) atom $R^3$ is a cross-link —E—Y—E—, wherein one end of the cross-link bonded to a second polymeric unit; each E is a divalent group selected from —CH2CH2— or —CH=CH— and Y is a divalent hydrocarbon group, a siloxane or any combination of these; and a is 265 to 2000, b is 0 to 249 and c is 1 to 250 with the provision that b+c≦250 and (B) a diluent.

2. The elastomer composition as claimed in claim 1 wherein $R^1$ is methyl.

3. The elastomer composition as claimed in claim 1 wherein Y is divalent hydrocarbon group.

4. The elastomer composition as claimed in claim 1 wherein $R^3$ is selected from, pentylene, hexylene, heptylene, octylene, nonylene, decylene, dodecylene, tetradecylene and mixtures thereof.

5. The elastomer composition as claimed in claim 1 wherein a has a value of 350 to 1000, b has a value of 0 to 100 and c has a value of 1 to 100 with the provision that b+c≦100.

6. The elastomer composition as claimed in claim 1 wherein $R^3$ is bonded into a second polymeric unit having the formula

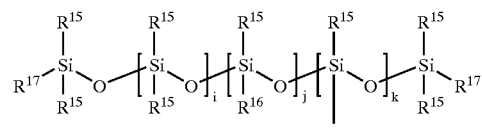

wherein each $R^{15}$, $R^{16}$, and $R^{17}$ is independently selected from hydrogen or a monovalent hydrocarbon group having 1 to 30 carbon atoms; and i is 0 to 2000, j is 0 to 250 and k is 1 to 250.

7. The elastomer composition as claimed in claim 1 wherein the silicone elastomer contains 0.01 to 90 mole % cross-links.

8. The elastomer composition as claimed in claim 1 wherein the silicone elastomer contains 1 to 20 mole % cross-links.

9. The elastomer composition as claimed in claim 1 wherein the silicone elastomer contains 10 to 40,000 of the first and second polymeric units.

10. The elastomer composition as claimed in claim 1 wherein the diluent is selected from silicones, organic oils, organic solvents and mixtures thereof.

11. The elastomer composition as claimed in claim 1 wherein the weight ratio of (A):(B) is from 1:100 to 10:1.

12. The elastomer composition as claimed in claim 11 wherein the weight ratio of (A):(B) is from 1:50 to 2:1.

13. The elastomer composition as claimed in claim 11 wherein the weight ratio of (A):(B) is from 1:20 to 1:1.

14. The elastomer composition as claimed in claim 10 wherein the diluent is a silicone.

15. A method for making an elastomer composition comprising (1) reacting in the presence of a hydrosilylation catalyst
  (a) a≡Si—H containing polysiloxane having the formula

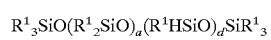

where each $R^1$ is independently a monovalent hydrocarbon group having 1 to 30 carbon atoms; a is 265 to 2000; and d is 1 to 250; with (b) diene, diyne or ene-yne compound; wherein (a) and (b) are dispersed in (c) a diluent; and (2) continuing the reaction until a silicone elastomer is formed by crosslinking and addition of ≡Si—H across double bonds in the diene, diyne or ene-yne compound.

16. The method as claimed in claim 15 wherein there is also present a second ≡Si—H containing polysiloxane selected from $HR^1{}_2SiO(R^1{}_2SiO)_eSiR^1{}_2H$, $HR^1{}_2SiO(R^1{}_2SiO)_a(R^1HSiO)_dSiR^1{}_2H$ and mixtures thereof where each $R^1$ is independently a monovalent hydrocarbon group having 1 to 30 carbon atoms; a is 265 to 2000; and d is 1 to 250, and e is 0 to 250 wherein the second ≡Si—H containing polysiloxane and the ≡Si—H containing polysiloxane are present in a mole ratio of >0 to 20.

17. The method as claimed in claim 15 wherein (b) is a diene compound.

18. The method as claimed in claim 15 wherein (b) is selected from 1,4-pentadiene, 1,5-hexadiene; 1,6-heptadiene; 1,7-octadiene, 1,8-nonadiene, 1,9-decadiene, 1,11-dodecadiene, 1,3-tetradecadiene, and 1,19-eicosadiene, 1,3 butadiyne, 1,5 hexadiyne (dipropargyl), and 1-hexene-5-yne.

19. The method as claimed in claim 15 wherein the diluent (c) is selected from silicones, organic oils, organic solvents and mixtures thereof.

20. The method as claimed in claim 19 wherein the diluent (c) is a silicone.

21. The method as claimed in claim 15 wherein (a) and (b) are present in a mole ratio of (a):(b) in the range of 0.7:1 to 1.3:1.

22. The method as claimed in claim 15 wherein the elastomer composition is crumbled into a silicone powder using mechanical force.

23. The method as claimed in claim 22 wherein the silicone powder has a particle size of 0.01 to 10000 micrometers.

24. The method as claimed in claim 15 of this invention wherein the elastomer composition is combined with a second diluent using shear force to produce a base composition.

25. A base composition comprising (A) the elastomer composition as claimed in claim 1 and (B) a second diluent.

26. The base composition as claimed in claim 25 wherein the second diluent is selected from silicones, organic oils, organic solvents and mixtures thereof.

27. The base compositions as claimed in claim 25 wherein there is 5 to 98 weight percent of second diluent based on the weight of the elastomer composition and second diluent.

28. A personal care product comprising (1) the silicone elastomer as claimed in claim 1 and (2) at least one personal care product ingredient.

29. The personal care product as claimed in claim 28 wherein the personal care product ingredient is selected from ester waxes, oils and fats of animal or vegetable origin, fatty alcohols, fatty acids, alkyl esters of fatty acids; hydrocarbon oils and waxes; water, organic solvents, perfumes, surfactants, oil-soluble vitamins, water-soluble vitamins, oil-soluble drugs, water-soluble drugs, actives and pharmaceutical compounds.

30. A product containing the elastomer composition of claim 1 chosen from antiperspirants, deodorants, skin creams, skin care lotions, moisturizers, facial treatment products, facial cleansing products bath oils, perfumes, colognes, sachets, sunscreens, pre-shave lotions, after-shave lotions, liquid soaps, body washes, bar soaps, shaving soaps, shaving lathers, hair shampoos, hair conditioners, hair colorants, hair sprays, mousses, permanents, depilatories, cuticle coats, make-ups, color cosmetics, foundations, blushes, lipsticks, lip balms, eyeliners, mascaras, eye shadows, oil removers, cosmetic removers, and delivery systems for oil and water soluble substances.

* * * * *